United States Patent [19]

Atallah et al.

[11] Patent Number: 5,445,962
[45] Date of Patent: Aug. 29, 1995

[54] NEW MICROORGANISMS

[76] Inventors: Yousef H. Atallah, 411 Helena Ave., Mt. Prospect, Ill. 60056; Robert G. Butz, 280 Springhill Dr. - Apt. 212, Roselle, Ill. 60172; James P. Krueger, 14527 S. Clifton Park, Midlothian, Ill. 60445

[21] Appl. No.: 229,035

[22] Filed: Aug. 5, 1988

[51] Int. Cl.$^6$ .............................................. C12N 1/20
[52] U.S. Cl. .................................. 435/252.1; 435/170; 435/253.3; 435/874; 435/262
[58] Field of Search ...................... 435/253.3, 874, 170, 435/252.1, 262

[56] References Cited

U.S. PATENT DOCUMENTS 4,816,403  3/1989  Roy .................................. 435/253.3

OTHER PUBLICATIONS

"ATCC Catalogue of Bacteria & Bacteriophages" 17th Ed. 1989, Ed. Gherna et al. pp. 136, 165–182.

J. Krueger, "Development of a Microbe for Degradation of Dicamba", Thesis, Illinois Institute of Technology, 1984.

J. Krueger, et al. "Isolation and Identification of Microorganisms for Degradation of Dicamba", Poster Presentation, Amoco–University, Naperville, Ill. (1987).

J. Krueger, et al., "Dicamba Degrading Microorganisms for Dicamba Susceptible Plants" Abstract for Soc. Ind. Microb. Annual Mtg. (1988).

Ferrer, et al. "Utilization of dicamba by soil bacteria" Agrochimica, vol. XXX, No. 6, Dec. 1986, pp. 458–464.

Ferrer, et al., "Ability of O–Anisate Degrading Microorganisms to Cometabolize DICAMBA", Chemisphere 14(10), 1645–48/1985.

Smith, et al. Chemical Abstracts, vol. 83, No. 3 (23373b).

*Primary Examiner*—Herbert J. Lilling
*Attorney, Agent, or Firm*—Allen E. Norris

[57] ABSTRACT

Dicamba degrading bacterial microorganisms are represented by the Pseudomonas and Moraxella ATCC deposits Nos. 53539, 53540 and 53541 and are characterized by morphologically appearing as short rounded rods and being capable of growing as a pure culture in sterile aqueous media in the presence of dicamba as essentially the sole carbon source.

4 Claims, No Drawings

NEW MICROORGANISMS

This invention relates to microorganisms capable of degrading dicamba (3,6-dichloro-o-anisic acid). In addition, this invention relates to procedures for obtaining these organisms and utilizing them to degrade dicamba from locations where its presence would be that of a contaminant or undesired toxicant.

Dicamba is an important herbicide. Like most important organic chemical compounds there are times when it can become an undesired contaminant due to misapplication, spills, mistakes in disposal or other like reasons. The presence of dicamba in the soil of a crop locus as a result of its application to combat weeds therein can also result in limitations on the use of the soil and dicamba itself. Consequently, there is a need for procedures and materials that will permit the ready removal of dicamba, and particularly for a means of removing dicamba from soil and aquatic environments.

It is therefore an object of this invention to provide methods and materials for the removal of dicamba from sites where its presence is undesired.

It is another object of this invention to provide microorganisms which will degrade dicamba to environmentally acceptable materials.

Other objects of this invention will become apparent from the ensuing description.

In accordance with the present invention, we have found that certain bacterial microorganisms after exposure to dicamba in a suitable growth environment such as pond sediment are capable of harboring and expressing genes which degrade dicamba and are also capable of growth reproduction in a practical fashion in aqueous cultures. In particular, the microorganisms of the present invention are bacteria characterized by morphologically appearing as short rounded rods and by being capable of growing as pure cultures in sterile aqueous media in the presence of dicamba (eg. 1000 ppm dicamba free acid) as essentially the sole carbon source.

The ability of the bacteria of the invention to grow in the presence of dicamba as essentially the sole carbon source indicates their capability of fulfilling the desired utility of degrading dicamba in an effective manner. Advantageously, the bacteria of the invention will degrade dicamba in both soil and in aquatic environments and are capable of growth as pure cultures in sterile aqueous liquid media in the presence of dicamba. Accordingly, the bacteria of the invention can be reproduced or grown in a practical manner for large scale use. Biologically pure cultures of these bacteria are also provided by the present invention.

Other advantageous and uses of the bacteria of the invention will be evident from the description hereinafter.

Representative of the bacteria of the invention are those of the genuses Pseudomonas and Moraxella.

Cultures of three microorganisms representing the present invention have been deposited with the American Type Culture Collection, Rockville, Md. The three microorganisms are identified below along with their identifying ATCC numbers (all deposited Sep. 11, 1986):

TABLE 1

| STRAIN # | GENUS | SPECIES | ATCC NO. |
|---|---|---|---|
| DI-6 | Pseudomonas | — | 53540 |
| DI-7 | Moraxella | — | 53539 |
| DI-8 | Pseudomonas | — | 53541 |

The present invention includes the progeny of said microorganisms and all naturally occurring and man-induced mutations thereof and their progeny which retain the fundamental characteristics recited above for the microorganisms of the invention.

The following examples demonstrate the isolation, identification, growth and certain evaluations of the above-identified bacterial strains which represent the present invention. In the examples, the $^{14}$C-dicamba had a radiochemical purity greater than 98% (U-phenyl label) and a specific activity of 11.5 mCi/m.mole. Optifluor (Packard Instrument Co.) was used as scintillation cocktail for total radiocarbon assays. Stock solutions of dicamba were prepared by titration with sodium hydroxide to pH 7.0. All chemical stock solutions were filter sterilized before being added to sterile media.

EXAMPLE 1

ISOLATION OF THE MICROORGANISMS

Samples of sediment (a soil and water mixture) were obtained from the storm water retention pond of the dicamba manufacturing plant of the Sandoz Crop Protection Corporation at Beaumont, Tex. (pond exposure to dicamba about 25 years). 2.0 ml of such sediment was inoculated into standard a chlorine-free sterile liquid media (aqueous) containing 1000 ppm dicamba as a sole carbon source (final volume =25 ml). The sterile media is described below,

| CHEMICAL | CONTENT (Grams per Liter) |
|---|---|
| $K_2HPO_4 3H_2O$ | 1.826 |
| $KH_2PO_4$ | 1.870 |
| $(NH_4)_2HPO_4$ | 0.660 |
| $MgSO_4$ | 0.097 |
| $MnSO_4 H_2O$ | 0.025 |
| $FeSO_4 H_2O$ | 0.005 |
| $CaSO_4$ | 0.001 |
| L-ascorbic acid | 0.005 |
| Water | to 1.0 liter | which standard media had been adjusted to pH 7.0 by the addition of sodium hydroxide (0.1N). The cultures were incubated at 30° C. on a rotary shaker at 150 rpm for one week. A 2.0 ml aliquot of the one week old culture was inoculated into the standard sterile media containing 1000 ppm dicamba (final volume=25 ml), and then incubated on the shaker for one week as described. About twelve 2.0 ml. aliquots of this culture were plated out on a mix of agar and the solids content of the chlorine-free media containing 1000 ppm dicamba as a sole carbon source. After several days individual colonies were streaked onto 1000 ppm dicamba agar and incubated until colonies appeared. Individual colonies from these streak plate isolates were assigned strain numbers. They were propogated on the dicamba agar and checked for purity by examination at 2000X magnification after fixation and gram staining. Three different strains were identified, all were gram negative and appeared to be pure cultures. These organisms were identified using a Flow N/F test system (Flow Laboratories, Inc., McLean, Va.). The results of such identification are given below in Table 2.

TABLE 2
IDENTIFICATION OF DICAMBA ASSIMILATING STRAINS

| Test | DI-6 | DI-7 | DI-8 |
|---|---|---|---|
| Oxidase | + | + | + |
| Fluorescein | − | − | − |
| Glucose Fermentation | − | − | + |
| $N_2$ Gas | − | − | − |
| Pyocyanin | − | − | − |
| Growth at 42° C. | − | − | − |
| Glucose | + | − | + |
| Xylose | + | − | + |
| Mannitol | − | − | + |
| Lactose | + | − | + |
| Maltose | − | − | + |
| Acetamide | − | − | − |
| Esculin | + | − | − |
| Urea | − | − | − |
| DNASE | − | + | − |
| ONPG | − | − | − |
| $H_2S$ | − | − | − |
| Indole | − | − | − |
| Motility | − | − | − |
| Gram Stain | − | − | − |
| ATCC Designation | 53540 | 53539 | 53541 |
| Morphology | Short rounded rods | Short rounded rods | Short rounded rods |

EXAMPLE 2
GROWTH KINETICS OF DICAMBA DEGRADERS IN LIQUID CULTURE

Each of the dicamba degrading organisms (DI-6, DI-7 and DI-8) was grown on the standard sterile liquid media to which was added 1000 ppm dicamba. Forty ml. of each culture was used to again inoculate the standard media containing 1000 ppm dicamba and 10 uCi of $^{14}C$-dicamba (final volume=500 ml). Cultures were incubated at 30° C. on a rotary shaker. All cultures were sampled at 0 time and at 6, 24 and 30 hours. At each sampling time, samples were diluted and plated out on nutrient agar to determine total viable cells present. The absorbance spectrum of undiluted samples between 190 nm to 750 nm was determined on a Perkin-Elmer model 552A UV/VIS scanning spectrophotometer. The absorbance at 600 nm was used as a standard measure of turbidity to determine growth. An aliquot of medium was acidified with 10% sulfuric acid and one-tenth ml was radioassayed in duplicate. All liquid scintillation counting was done in a Searle Mark III 6880 Liquid Scintillation Spectrometer using an external standard quench correction program. Appropriate background counts were substracted from all samples. The results and analysis are revealed in Table 3. Chloride release (about 97%) was determined by the method of Bergmann and Sanik, Analytical Chemistry 29:241-243 (1957). The absorbance at 274 nm decreased to non-detectable levels indicating essentially complete dicamba removal (Table 3). A plot (not shown) of the percent removal of soluble $^{14}C$ from the liquid media versus culture time indicated that up to 80% of the substrate carbon is converted to carbon dioxide. The substrate carbon remaining in the media was probably incorporated into cell biomass since cell number and turbidity increased. Generation times (cell doubling times) were calculated during the log phase of growth and were as follows: Strain DI-6, 4.5 hrs.; Strain DI-7, 3.5 hrs.; Strain DI-8, 6.2 hrs.

TABLE 3
Growth Kinetics of Dicamba Degrading Organisms in Liquid Culture Containing 1000 ppm Dicamba.

| Strain | Time (hrs) | Viable Cells per ml | Abs600 | Abs274[d] | ppm Dicamba[a][e] | Total Chloride (ppm) | % Removal Dicamba[b] | DPM/ml Acidified media | % Removal Dicamba[c] |
|---|---|---|---|---|---|---|---|---|---|
| DI-6 | 0 | $2.1 \times 10^8$ | 0.03 | 2.36 | 818 | 0 | 0 | 56,540 | 0 |
|  | 6 | $7.5 \times 10^8$ | 0.03 | 2.38 | 828 | 26 | 8.1 | 52,040 | 8.0 |
|  | 24 | $1.3 \times 10^8$ | 0.14 | NP | ND | 325 | 101.2 | 13,520 | 76.1 |
|  | 30 | $6.8 \times 10^8$ | 0.13 | NP | ND | 334 | 104.0 | 14,360 | 74.6 |
| DI-7 | 0 | $7.8 \times 10^8$ | 0.02 | 2.38 | 827 | 0 | 0 | 56,300 | 0 |
|  | 6 | $8.5 \times 10^8$ | 0.02 | 2.56 | 887 | 15 | 4.7 | 55,710 | 1.0 |
|  | 24 | $9.8 \times 10^8$ | 0.13 | NP | ND | 296 | 92.2 | 21,630 | 61.6 |
|  | 30 | $1.0 \times 10^8$ | 0.13 | NP | ND | 315 | 98.1 | 18,130 | 67.8 |
| DI-8 | 0 | $1.0 \times 10^8$ | 0.02 | 2.43 | 843 | 0 | 0 | 58,220 | 0 |
|  | 6 | $1.4 \times 10^8$ | 0.02 | 2.56 | 887 | 11 | 3.4 | 57,490 | 1.3 |
|  | 24 | $1.1 \times 10^8$ | 0.07 | NP | ND | 151 | 47.0 | 40,120 | 31.1 |
|  | 30 | $1.0 \times 10^8$ | 0.13 | NP | ND | 290 | 90.3 | 23,440 | 59.7 |

[a]Based on Absorbance at 274 nm
[b]Based on Chloride release
[c]Based on Soluble $^{14}C$ in the media
[d]NP means no peak
[e]ND means not detectable

EXAMPLE 3
EFFECT OF pH ON DICAMBA DEGRADING ACTIVITY

Four ml of each of the three dicamba degrading cultures (each 3 days old) was used to inoculate standard liquid media containing 1000 ppm dicamba and 10 uCi of $^{14}$-dicamba at pH 4.0, 5.0, 6.0, 7.0 and 8.0 (final volume=50 ml). Cultures were incubated at 30° C. On a rotary shaker. All cultures were sampled at 0 time and 24 hours. Aliquots of media were radioassayed in duplicate. The effect of pH on dicamba degrading activity in liquid culture is shown below in Table 4.

TABLE 4
ACTIVITY OF DICAMBA DEGRADERS AT VARIOUS pH VALUES WITH PPM DICAMBA

| Strain | Initial pH | % Substrate Carbon Removed After 24 Hours |
|---|---|---|
| DI-6 | 4.0 | 1.6 |
|  | 5.0 | 21.5 |
|  | 6.0 | 38.9 |
|  | 7.0 | 61.6 |
|  | 8.0 | 61.1 |
| DI-7 | 4.0 | 0.0 |

TABLE 4-continued

ACTIVITY OF DICAMBA DEGRADERS AT
VARIOUS pH VALUES WITH PPM DICAMBA

| Strain | Initial pH | % Substrate Carbon Removed After 24 Hours |
|---|---|---|
|  | 5.0 | 1.0 |
|  | 6.0 | 37.0 |
|  | 7.0 | 70.0 |
|  | 8.0 | 66.0 |
| DI-8 | 4.0 | 31.8 |
|  | 5.0 | 31.0 |
|  | 6.0 | 30.7 |
|  | 7.0 | 65.6 |
|  | 8.0 | 66.0 |

All three organisms removed approximately the same amount of substrate $^{14}C$ at pH 7.0 and 8.0. The ability to remove substrate $^{14}C$ decreases when pH is decreased. However, Strain DI-8 was able to remove 31.8% of the substrate $^{14}C$ even at pH 4.0. The ability of these organisms to degrade dicamba over a wide range of pH values indicates usefulness for removing dicamba from a wide variety of aquatic and soil environments.

EXAMPLE 4

GROWTH KINETICS OF DICAMBA DEGRADERS IN SOIL $^{14}C$-Dicamba was mixed with sieved field moist Kenyon Loam soil to yield a concentration of 3.4 ppm dicamba in the soil. This is equivalent to an application rate of approximately 2 lb/acre when incorporated into two inches of soil. Enumeration of naturally occurring soil microorganisms in untreated field moist soil was conducted by weighing out 10 g. of soil into 90 ml of sterile water. Dilutions were plated out on nutrient agar to enumerate bacteria, actinomycete agar for enumeration of actinomycetes, and potato dextrose agar for enumeration of fungi. Characteristics of the Kenyon Loam soil are presented below:

| | |
|---|---|
| % Organic Carbon | 2.2 |
| % Organic Matter (Calculated from % Organic Carbon) | 3.8 |
| Cation exchange capacity (meg/100 g) | 20.4 |
| pH (in deionized water) | 6.2 |
| pH (in 0.01M $CaCl_2$) | 6.0 |
| 75% of 0.33 bar level (g. of water/100 g. dry soil) | 24.4 |
| % Sand | 34.0 |
| % Silt | 41.0 |
| % Clay | 25.0 |
| Bacteria per gram of soil | $6.30 \times 10^5$ |
| Actinomycetes per gram of soil | $2.60 \times 10^5$ |
| Fungi per gram of soil | $3.20 \times 10^4$ |
| Total Number of organisms per gram of soil | $9.22 \times 10^5$ |

Treated soil (62.2, g. moist soil equivalent to 50 g. dry) was added to 125 ml amber serum bottles. Duplicates of treated soil were inoculated with 1.0 ml of culture from Strain DI-6, DI-7 or DI-8. All three strains had been grown for two days on 1000 ppm dicamba and then concentrated to 5.0 ml with centrifugation (10 minutes at $2500 \times G$). Viable cell counts were conducted on inoculums so that the total number of cells added to the treated soil could be determined. A bottle of the treated soil inoculated with 1.0 ml of water served as the control. All soil treatments resulted in soil moistures that were 75% of the 0.33 bar level. All bottles were sealed with teflon septums and incubated at 25° C. At 1, 3, 7, 14 and 21 days all samples were flushed with $CO_2$-free air to insure maintenance of an aerobic state. Exit air was bubbled through 1.5N KOH to trap $^{14}CO_2$. One-half ml of KOH was radioassayed in duplicate. As revealed in Table 5, below, an average of 63.7% of the, dicamba applied to soil was metabolized to carbon dioxide in the inoculated soils, compared to only 2.2% in the uninoculated soil after 21 days.

TABLE 5

METABOLISM OF $^{14}C$-DICAMBA (3.4 PPM)
IN SOIL BY DICAMBA DEGRADERS
Cumulative % of Applied Radiocarbon
Metabolized to Carbon Dioxide

| Time (days) | uninoc. control | Strain DI-6 | Strain DI-7 | Strain DI-8 |
|---|---|---|---|---|
| 1 | 0.2 | 33.2 | 35.7 | 28.9 |
| 3 | 0.9 | 47.9 | 45.7 | 36.6 |
| 7 | 1.2 | 55.5 | 52.5 | 52.8 |
| 14 | 1.9 | 64.9 | 60.0 | 62.5 |
| 21 | 2.2 | 66.5 | 60.8 | 63.7 |

Soil from one sample of each of the 21 day inoculated soils were analyzed for dicamba and 3,6-dichlorosalicylic acid according to a gas chromatography (GC) residue method for these substances. Recovery and check samples were also analyzed. The highest degradation rates occurred between 0 and 1 day in all of the inoculated treatments. The GC analysis indicates nearly complete removal (>99%) of dicamba and greatly reduced accumulation of 3,6-dichlorosalicylic acid after 21 days, as shown in Table 6, below. Initial inoculum size (in cells/gram of field moist soil) for each strain, and the percent of total organisms this represents are as follows: Strain DI-6, $6.96 \times 10^8$, 99.7%; Strain DI-7, $2.37 \times 10^8$, 99.6%; Strain DI-8, $2.69 \times 10^8$, 99.7%.

TABLE 6

GC ANALYSIS OF DICAMBA
TREATED SOIL 21 DAYS AFTER INOCULATION
WITH DICAMBA DEGRADING ORGANISMS

| Inoculum | Dicamba (ppm) | 3,6-dichloro-salicylic acid (ppm) |
|---|---|---|
| DI-6 | ND[a] | 0.014 |
| DI-7 | 0.019 | 0.075 |
| DI-8 | 0.067 | 0.260 |
| Control | 2.250 | 0.670 |

[a]Not Detectable, Limit of Detection for dicamba and 3,6-dichlorosalicylic acid was 0.01 ppm The results in the experiment of Example 4, above, also indicate that 3,6-dichlorosalicylic; acid, the apparent first stage degradation product from the treatment of dicamba with the microorganisms of the invention, is itself degraded by such microorganisms and that the final result is substantially complete degradation of the organic constitution of the dicamba molecule. Accordingly, the invention also provides a method for degrading 3,6-dichlorosalicylic acid in a soil or aqueous media comprising dispersing into said media a 3,6-dichlorosalicylic acid degrading effective amount of a bacteria microorganism of the present invention.

EXAMPLE 5

PROPAGATION, PRESERVATION, AND VIABILITY OF DICAMBA DEGRADERS

Strains DI-6, DI-7, and DI-8 were grown in a Queue Fermenter (Parkersburg, W. Va.) on the previously described 1000 fermenter was set to maintain the temperature at 30° C. and provide an agitation speed of 250 rpm. An airflow of 1.0 standard liters per minute maintained a dissolved oxygen concentration of greater than 95% saturation for all cultures. After 3 days each five liter culture was concentrated to 50 ml. Aliquots were diluted and plated out on nutrient agar to determine the number of viable cells present. Two ml of each concentrate was: (1) frozen, (2) frozen with an equal volume of glycerol, or (3) freeze-dried. All samples were sealed and stored at −70° C. Samples of each culture were thawed or reconstituted at 0 time and at 1, 6 and 12 months. The number of viable cells present was determined. Cultures were inoculated into 25 ml of the 1000 ppm dicamba sterile liquid media to determine if the ability to degrade dicamba was still present. Inoculated media was radioassayed at 0 time and 24 hours to determine if dicamba was being metabolized. The thawed and reconstituted strains DI-6, DI-7, and DI-8 were able to grow in a bench scale (5 liter) fermentor. The pH of the cultures decreased from an initial pH of 7.0 to 6.3 as dicamba was metabolized. Culture viability and dicamba degrading activity after such preservation are given in Table 7, below.

TABLE 7

CULTURE VIABILITY AND DICAMBA DEGRADING ACTIVITY AFTER PRESERVATION

| Strain | Time (months) | % Viability after freezing | % Viability after freezing with glycerol | % Viability after freeze-drying | Growth in 1000 ppm Dicamba media |
|---|---|---|---|---|---|
| DI-6 | 0 | 51.6 | 9.5 | 5.8 | + |
| | 1 | 24.8 | 11.6 | 6.5 | + |
| | 6 | 4.1 | 1.3 | 2.0 | + |
| | 12 | 0.5 | 0.7 | 0.3 | + |
| DI-7 | 0 | 19.7 | 26.6 | 2.0 | + |
| | 1 | 20.0 | 13.2 | 0.2 | + |
| | 6 | 7.1 | 7.4 | 0.2 | + |
| | 12 | 12.8 | 1.6 | 0.03 | + |
| DI-8 | 0 | 15.7 | 0.2 | 40.7 | + |
| | 1 | 1.3 | 0.5 | 0.3 | + |
| | 6 | 4.2 | 0.2 | 0.2 | + |
| | 12 | 1.5 | 0.8 | 0.7 | + |

As shown in Table 7, cultures that were frozen for up to one year demonstrated an ability to survive and in certain cases even showed the best survival rates. Cultures where less than 1% of the cells survived still showed the ability to degrade dicamba in liquid culture. Preserving viable cultures of dicamba degraders is a desirable factor in developing inoculums for practical use. The ability to propagate dicamba degrading strains as biologically pure cultures in large volumes is also particularly useful for the production of large amounts of inoculums.

EXAMPLE 6

DEGRADING DICAMBA IN SOIL TO BENEFIT CROP GROWTH

Experiments were conducted in a growth chamber to demonstrate the use of the dicamba degraders of the invention in removing phytotoxic dicamba from soil in which a crop plant is desired to be planted. Cups (6.5 cm diameter, 4 oz.) were filled with Wisconsin clay loam. Individual cups were given a dicamba treatment by pipetting a dicamba-containing composition evenly on the soil, followed by mixing of the soil in the cups. Dicamba treated soil contained dicamba in an amount equivalent to a field application at the rate of 0.5, 4 and 8 pounds/acre. Each concentration for each experiment was replicated seven times for cups to be inoculated while each control which was not to be inoculated was replicated ten times. Fourteen (14) days after dicamba treatment the cups were inoculated with a 2.0 ml. centrifuge-concentrated aqueous culture (concentrated from 1 liter to about 60 ml.) of one of the three dicamba degraders DI-6, DI-7 and DI-8 (see Example 4) sufficient to give a cell concentration of the dicamba degrader of average about $7.9 \times 10^7$ cells per gram of soil. The cups were then placed in the growth chamber at a constant 15° C. and each cup planted with pea seeds at various given times after the inoculation as indicated in the following Tables 8, 9 and 10 (0, 2 and 5 days time, respectfully). The resulting number of germinations of the seeds and the weight of the resulting plants (weight of leaves and stems, of the roots and total weight) were recorded. Cups were watered as necessary to maintain the initial moisture level. Each of the individual dicamba degraders DI-6, DI-7 and DI-8 were evaluated in these tests. The results are given below in Tables 8, 9 and 10.

TABLE 8

Results of growth chamber experiment with dicamba-treated soil and dicamba degraders. Soil was inoculated with dicamba degrading microbes 14 days after dicamba application. Pea seeds were planted immediately after inoculation. Seedlings were harvested and weighed 21 days after inoculation.

| Dicamba Rate (lb/acre) | Dicamba Degrader Strain | Weight of Leaves and Stems (g) | Weight of Roots (g) | Total Weight (g) | % Germination |
|---|---|---|---|---|---|
| 0 | DI-6 | 2.22 | 3.18 | 5.40 | 88 |
| | DI-7 | 2.22 | 2.69 | 4.91 | 100 |
| | DI-8 | 2.78 | 2.59 | 5.37 | 100 |
| | uninoculated | 1.84 | 2.36 | 4.20 | 63 |
| 0.5 | DI-6 | 1.74 | 1.81 | 3.55 | 63 |
| | DI-7 | 2.35 | 2.45 | 4.80 | 100 |
| | DI-8 | 2.18 | 2.56 | 4.74 | 100 |
| | uninoculated | 0 | 1.08 | 1.08 | 0 |
| 4.0 | DI-6 | 0 | 1.17 | 1.17 | 25 |
| | DI-7 | 0 | 1.17 | 1.17 | 13 |
| | DI-8 | 0.43 | 1.98 | 2.41 | 38 |
| | uninoculated | 0 | 1.18 | 1.18 | 13 |
| 8.0 | DI-6 | 0 | 1.07 | 1.07 | 25 |
| | DI-7 | 0 | 0.64 | 0.64 | 0 |
| | DI-8 | 0 | 0.82 | 0.82 | 0 |
| | uninoculated | 0 | 0.62 | 0.62 | 0 |

TABLE 9

Results of growth chamber experiment with dicamba-treated soil and dicamba degraders. Soil was inoculated with dicamba degrading microbes 14 days after dicamba application. Pea seedlings were planted 2 days after inoculation. Seedlings were harvested and weighed 19 days after inoculation.

| Dicamba Rate (lb/acre) | Dicamba Degrader Strain | Weight of Leaves and Stems (g) | Weight of Roots (g) | Total Weight (g) | % Germination |
|---|---|---|---|---|---|
| 0 | DI-6 | 1.54 | 2.55 | 4.09 | 50 |
| | DI-7 | 1.73 | 2.39 | 4.12 | 25 |
| | DI-8 | 2.69 | 3.02 | 5.71 | 100 |
| | uninoculated | 1.60 | 2.16 | 3.76 | 50 |
| 0.5 | DI-6 | 1.35 | 1.70 | 3.05 | 50 |
| | DI-7 | 2.08 | 2.70 | 4.78 | 100 |
| | DI-8 | 1.92 | 2.24 | 4.16 | 100 |
| | uninoculated | 0.11 | 1.20 | 1.31 | 25 |
| 4.0 | DI-6 | 1.15 | 2.70 | 3.85 | 75 |
| | DI-7 | 1.76 | 2.46 | 4.22 | 100 |

TABLE 9-continued

Results of growth chamber experiment with dicamba-treated soil and dicamba degraders. Soil was inoculated with dicamba degrading microbes 14 days after dicamba application. Pea seedlings were planted 2 days after inoculation. Seedlings were harvested and weighed 19 days after inoculation.

| Dicamba Rate (lb/acre) | Dicamba Degrader Strain | Weight of Leaves and Stems (g) | Weight of Roots (g) | Total Weight (g) | % Germination |
|---|---|---|---|---|---|
|  | DI-8 | 1.98 | 2.51 | 4.49 | 100 |
|  | uninoculated | 0 | 1.61 | 1.61 | 0 |
| 8.0 | DI-6 | 0.99 | 2.22 | 3.21 | 50 |
|  | DI-7 | 1.67 | 1.48 | 3.15 | 100 |
|  | DI-8 | 1.61 | 2.11 | 3.72 | 50 |
|  | uninoculated | 0 | 0.85 | 0.85 | 0 |

TABLE 10

Results of growth chamber experiment with dicamba-treated soil and dicamba degraders. Soil was inoculated with dicamba degrading microbes 14 days after dicamba application. Pea seedlings were planted 5 days after inoculation. Seedlings were harvested and weighed 16 days after inoculation.

| Dicamba Rate (lb/acre) | Dicamba Degrader Strain | Weight of Leaves and Stems (g) | Weight of Roots (g) | Total Weight (g) | % Germination |
|---|---|---|---|---|---|
| 0 | DI-6 | 2.07 | 2.71 | 4.78 | 75 |
|  | DI-7 | 1.28 | 1.66 | 2.94 | 50 |
|  | DI-8 | 1.37 | 2.08 | 3.45 | 75 |
|  | uninoculated | 2.06 | 2.71 | 4.77 | 100 |
| 0.5 | DI-6 | 2.44 | 3.18 | 5.62 | 100 |
|  | DI-7 | 2.36 | 2.36 | 4.72 | 100 |
|  | DI-8 | 1.38 | 1.79 | 3.17 | 75 |
|  | uninoculated | 0.83 | 2.03 | 2.86 | 50 |
| 4.0 | DI-6 | 1.38 | 2.51 | 3.89 | 75 |
|  | DI-7 | 1.59 | 1.99 | 3.58 | 75 |
|  | DI-8 | 0 | 1.90 | 1.90 | 25 |
|  | uninoculated | 0 | 1.34 | 1.34 | 0 |
| 8.0 | DI-6 | 1.04 | 1.95 | 2.99 | 25 |
|  | DI-7 | 1.80 | 2.08 | 3.88 | 75 |
|  | DI-8 | 2.02 | 2.62 | 4.64 | 100 |
|  | uninoculated | 0 | 1.13 | 1.13 | 0 |

As shown by Tables 8, 9 and 10, all three of the dicamba degraders protected the peas from dicamba at the 0.5 pound/acre dicamba rate when the seeds were planted immediately after inoculation. When the peas were planted only two or more days after inoculation, the dicamba degrading bacteria of the invention also protected the peas from the dicamba at the higher 4.0 and 8.0 pound per acre rates, even though the soil had been treated with the dicamba only about two weeks before planting. These results indicate that, in addition to general usefulness in removing dicamba from soil and aquatic environments, the dicamba degrading bacteria may be also employed to permit the use of dicamba in the planting season to combat weeds in soils to be planted with dicamba sensitive crops.

EXAMPLE 7

Preliminary tests to demonstrate Dicamba degrading ability of the microorganisms of the invention in the field were carried out in 2×4 foot test plots (48 total plots) on a farmland in Elburn, Ill. (soil conditions: 24% sand, 50% silt, 26% clay and 4.4% organic, pH 4.8). On day one (May 5th), different plots were treated with dicamba at 0.5, 2.0 and 8.0 lb/acre rates assigned the identifications B, C and D respectively (the non-treated Control being A). Nineteen (19) days later the microorganism strains DI-6, DI-7 and DI-8 were applied to various plots (estimated to yield 200,000 organisms per gram of soil from an inoculation of cultures prepared as in Example 5 and involving 15 liters grown with 1000 ppm dicamba followed by centrifuging, washing and freezing at minus 70° C. until used). One plot at each dose level was left uninoculated as a control. Various plots were planted with soybeans (a dicamba sensitive crop) on the day of inoculation and 7 and 32 days after inoculation. Plants were harvested in mid October and 4 inches of rain in one day were experienced in mid August. The plants were evaluated and average results in each plot determined in terms of a) number of emerged plants (No.); b) the weight of leaves, stems and roots (Wt.); and c) height of the plant (Hgth). The results which are shown in Table 11 below indicate the ability of the microorganisms to retard the adverse effects of dicamba under various conditions.

TABLE 11

Field Test - Plot Results

| Treatment | 0-Days No. | 0-Days Wt. | 0-Days Hgth. | 7-Days No. | 7-Days Wt. | 7-Days Hgth. | 32-Days No. | 32-Days Wt. | 32-Days Hgth. |
|---|---|---|---|---|---|---|---|---|---|
| A-Control | 10.6 | 5.9 | 38.08 | 5.0 | 3.17 | 31.5 | 6.33 | .75 | 17.64 |
| A-DI-6 | 8.3 | 4.3 | 38.14 | 8.0 | 3.58 | 38.66 | 5.0 | .83 | 11.34 |
| A-DI-7 | 8.3 | 3.7 | 37.48 | 8.3 | 4.17 | 36.95 | 2.17 | .04 | 8.47 |
| A-DI-8 | 6.3 | 3.1 | 38.19 | 8.0 | 4.5 | 35.34 | 8.3 | 1.57 | 20.78 |
| B-Control | 8.3 | 3.3 | 33.36 | 7.0 | 3.08 | 35.44 | 7.3 | 1.75 | 22.95 |
| B-DI-6 | 7.7 | 4.4 | 41.30 | 7.3 | 3.08 | 31.43 | 4.3 | .40 | 15.13 |
| B-DI-7 | 9.67 | 4.67 | 37.46 | 7.0 | 3.67 | 37.51 | 8.0 | 1.0 | 17.6 |
| B-DI-8 | 7.3 | 3.8 | 34.25 | 8.7 | 4.17 | 35.85 | 7.66 | 1.0 | 16.40 |
| C-Control | 7.6 | 2.9 | 40.37 | 8.7 | 4.3 | 38.8 | 5.0 | 6.66 | 20.03 |
| C-DI-6 | 8.0 | 3.4 | 37.16 | 7.67 | 3.8 | 37.62 | 4.66 | 0.12 | 11.59 |
| C-DI-7 | 7.3 | 3.15 | 37.92 | 8.0 | 3.67 | 37.02 | 3.66 | 0.58 | 17.66 |
| C-DI-8 | 8.1 | 3.9 | 36.24 | 7.3 | 3.9 | 36.55 | 6.33 | 0.66 | 16.88 |
| D-Control | 0 | 0 | 0 | 0 | 0 | 0 | 0 | 0 | 0 |
| D-DI-6 | 3.0 | 2.08 | 32.58 | 4.67 | 3.37 | 27.70 | 8.33 | 1.56 | 16.38 |
| D-DI-7 | 0 | 0 | 0 | 1.67 | .03 | 3.22 | 2.66 | .03 | 5.27 |
| D-DI-8 | 0 | 0 | 0 | 0 | 0 | 0 | 1.6 | .01 | 5.5 |

Note: The A-Control involved the three plots not treated with either herbicide or microorganism.

Microorganisms may also be characterized by whole cell fatty acid content in accordance with the procedure described by L. Miller et al., Bacteria Identification By Gas Chromatography of Whole Cell Fatty Acids, Application Note 228-41 (1985), available from the Hewlett-Packard Company. An evaluation of DI-6, DI-7 and DI-8 by this method provided the results given below in Table 12.

TABLE 12

| Fatty Acid | Pseudomonas sp. DI-6 Peak Area % | Moraxella sp. DI-7 | Pseudomonas sp. DI-8 |
|---|---|---|---|
| C10:0 | 3.5 | 3.6 | 3.8 |
| C12:0 | 3.4 | 3.3 | 4.3 |
| C12:0 20H | 3.6 | 3.7 | 3.6 |
| C12:0 30H | 4.3 | 4.3 | 4.9 |
| C14:0 | 0.5 | 0.5 | 0.6 |
| C16:1 cis9 | 39.2 | 35.4 | 35.0 |
| C16:1 trans9 | 0.0 | 0.0 | 0.0 |
| C16:0 | 29.6 | 30.6 | 29.0 |
| C17:0 cyclo | 0.5 | 4.1 | 2.9 |
| C18:0 | 0.4 | 0.3 | 0.0 |

TABLE 12-continued

| Fatty Acid | Pseudomonas sp. DI-6 | Moraxella sp. DI-7 | Pseudomonas sp. DI-8 |
|---|---|---|---|
| | Peak Area % | | |
| C18:1 trans9 | 0.0 | 0.0 | 0.0 |
| C19:0 cyclo | 0.0 | 0.0 | 0.0 |
| Unidentified | 15.0 | 14.1 | 16.0 |

The microorganisms of the present invention may be employed in other ways to protect crop plants from dicamba and expand the use dicamba at or about the planting time of crops. In particular, the microorganism may be employed as a seed coating to protect the germinating seed and resulting seedlings from dicamba which has been applied to a crop locus or which will be applied prior to crop emergence, more typically applied prior to planting. Methods for coating seeds with microorganisms are generally known and may be employed to protect seeds and seedling from dicamba in accordance with the invention. Certain such methods involve inoculating or mixing a suitable agriculturally acceptable solid carrier such as sterilized peat moss, diatomaceous earth and clay with a concentrated culture of the bacteria of the invention and coating the seeds with the resulting inoculated carrier. In some cases, such as with peat moss, a agriculturally acceptable surfactant may be included and the inoculated carrier mixed with water to form a liquid composition for coating the seeds, eg. by dipping. Such dips may be also conveniently employed at the farm site just prior to planting. Another method of seed coating which maybe employed simply involves coating the seeds with a concentrated aqueous culture of the bacteria of the invention followed by gentle drying of the resulting coated seeds. Substantially similar results may be obtained by planting untreated seed followed promptly by spraying or similar application of an aqueous composition containing an inoculated carrier such as the inoculated peat moss and surfactant combination into the seed hole or furrow. For all such seed protection purposes concentrated aqueous cultures such as described in the foregoing examples may be employed. Essentially any plant or crop seed may coated and protected by the dicamba-degrading bacteria of the invention. Particularly of interest are the seeds of soybeans, wheat and corn, especially soybeans.

The term Dicamba has been used hereinabove in a general way to indicate the free acid form of 3,6-dichloro-o-anisic acid although the mixing of such dicamba free acid with the sodium hydroxide neutralized sterile media in the Examples hereof results essentially in aqueous solutions of the sodium salt of 3,6-dichloro-o-anisic acid. It will be understood that the invention applies to degrading such 3,6-dichloro-anisic acid in both free acid and salt form, particularly including the herbicidally effective salt forms and especially the water soluble salt forms. Similarly, 3,6-dichlorosalicylic acid in free acid or salt form, especially including the water soluble salt forms, are degraded by the bacteria of the invention. Dicamba and its herbicidally effective salt forms have been often described in the literature and include without limitations those mentioned in U.S. Pat. Nos. 3,013,054 and 3,012,870.

What is claimed is:

1. A biologically pure culture of at least one bacterial microorganism characterized by appearing as short rounded rods and capable of growing in sterile aqueous media in the presence of 3,6-dichloro-o-anisic acid as essentially the sole carbon source and being selected from the group consisting of ATCC 53539, ATCC 53540, ATCC 53541 and mutants thereof.

2. A microorganism according to claim 1, which is selected from the group consisting of ATCC 53539, ATCC 53540, ATCC 53541.

3. A microorganism according to claim 1 which is ATCC 53540 or a mutant thereof.

4. A microorganism according to claim 2 which is ATCC 53540.

* * * * *